(12) United States Patent
Foley et al.

(10) Patent No.: US 10,073,070 B2
(45) Date of Patent: Sep. 11, 2018

(54) CHROMATOGRAPHY COLUMN

(71) Applicant: Waters Technologies Corporation, Milford, MA (US)

(72) Inventors: William G. Foley, North Andover, MA (US); Greg P. Murphy, Hopkington, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 268 days.

(21) Appl. No.: 14/433,396

(22) PCT Filed: Sep. 27, 2013

(86) PCT No.: PCT/US2013/062084
§ 371 (c)(1),
(2) Date: Apr. 3, 2015

(87) PCT Pub. No.: WO2014/055331
PCT Pub. Date: Apr. 10, 2014

(65) Prior Publication Data
US 2015/0276691 A1    Oct. 1, 2015

Related U.S. Application Data

(60) Provisional application No. 61/709,210, filed on Oct. 3, 2012.

(51) Int. Cl.
*G01N 30/86* (2006.01)
*B01D 15/08* (2006.01)
*G01N 30/88* (2006.01)
(Continued)

(52) U.S. Cl.
CPC ......... *G01N 30/8651* (2013.01); *B01D 15/08* (2013.01); *B01D 15/10* (2013.01);
(Continued)

(58) Field of Classification Search
CPC .............. G01N 30/86; G01N 30/8651; G01N 30/8655; G01N 30/88; G01N 2030/8804; G01N 2030/025; G01N 2035/00881
(Continued)

(56) References Cited

U.S. PATENT DOCUMENTS 5,434,971 A * 7/1995 Lysakowski, Jr. .... G06F 17/246
    702/31
6,001,953 A * 12/1999 Davis ..................... C08G 63/64
    528/196
(Continued)

FOREIGN PATENT DOCUMENTS

| WO | 2011/021198 A2 | 2/2011 |
| WO | 2011/043996 A1 | 4/2011 |
| WO | 2011/161481 A1 | 12/2011 |

OTHER PUBLICATIONS

International Search Report and Written Opinion dated Feb. 7, 2014, for Application No. PCT/US13/62084 (12 pages).

*Primary Examiner* — Benjamin Schmitt
(74) *Attorney, Agent, or Firm* — Schmeiser, Olsen & Watts LLP

(57) ABSTRACT

Chromatographic separation devices are described that include a chromatographic separation module and a memory component. The memory component is attached to the chromatographic separation module, contains information related to use history of the chromatographic separation module with respect to the entire lifetime of the module, and includes a write-once-read-many (WORM) area where the information is written and where the information, once written, cannot be deleted or modified.

24 Claims, 3 Drawing Sheets

(51) Int. Cl.
*B01D 15/10* (2006.01)
*G01N 21/64* (2006.01)
*G01N 21/65* (2006.01)
*B01D 15/22* (2006.01)
*G01N 35/00* (2006.01)
*G01N 30/02* (2006.01)

(52) U.S. Cl.
CPC ............. *G01N 21/64* (2013.01); *G01N 21/65* (2013.01); *G01N 30/86* (2013.01); *G01N 30/88* (2013.01); *B01D 15/22* (2013.01); *G01N 2030/025* (2013.01); *G01N 2030/027* (2013.01); *G01N 2030/889* (2013.01); *G01N 2030/8881* (2013.01); *G01N 2035/00881* (2013.01)

(58) Field of Classification Search
USPC .............................................. 73/23.35, 23.36
See application file for complete search history.

(56) References Cited

U.S. PATENT DOCUMENTS

| | | | |
|---|---|---|---|
| 6,613,224 B1* | 9/2003 | Strand | G01N 30/6091 210/198.2 |
| 2001/0053429 A1* | 12/2001 | Je | C09B 23/10 428/64.4 |
| 2003/0036207 A1 | 2/2003 | Washburn et al. | |
| 2003/0120633 A1* | 6/2003 | Torre-Bueno | G06F 19/366 |
| 2007/0089484 A1 | 4/2007 | Bailey et al. | |
| 2009/0175766 A1 | 7/2009 | deCorral | |
| 2010/0280811 A1 | 11/2010 | Gorenstein et al. | |
| 2012/0028897 A1 | 2/2012 | Currie et al. | |
| 2012/1028897 | 2/2012 | Currie et al. | |
| 2013/0219999 A1* | 8/2013 | Casey | F04B 19/006 73/61.48 |

\* cited by examiner

CHROMATOGRAPHY COLUMN

RELATED APPLICATIONS

This application is the National Stage of International Application No. PCT/US2013/062084, filed on Sep. 27, 2013, which claims priority to and benefit of U.S. Provisional Patent Application No. 61/709,210 entitled "A Chromatography Column," filed Oct. 3, 2012. The contents and teachings of each of these applications are hereby expressly incorporated herein by reference in their entirety.

TECHNICAL FIELD

This disclosure generally relates to managing the lifetime data of a chromatographic separation device without need for an external storage device.

BACKGROUND

A chromatographic separation device, e.g., an analytical column, typically lasts tens of thousands of sample injections for its lifetime; each injection typically generates thousands of data points. Managing data generated during the entire lifetime of a chromatographic separation device proves a difficult challenge. Most common approaches nowadays include manually logging and tracking data and information of a separation device with paper notebooks, which is laborious, time consuming and prone to human errors. An external electronic device, e.g., an electronic laboratory notebook (ELN), can also be used to manage data of a separation device, which is, however, not an integral part of (and often has to be carried along with) the separation device, of which the information is being traced. Some separation devices have a memory component, which captures chromatographic data with respect to a limited number of sample injections, and once a device storage capacity is reached, the data stored on the device is overwritten.

SUMMARY

Some embodiments arise, in part, from the realization that a chromatographic separation device having a memory component and a data-processing component can advantageously be configured to manage data generated during the entire lifetime of the chromatographic separation device. Such embodiments store the lifetime data of the chromatographic separation device without need for an external storage device.

One embodiment characterizes a chromatographic separation device, which includes a chromatographic separation module and a memory component. The memory component is attached to the chromatographic separation module, contains information related to the chromatographic separation module with respect to the entire lifetime thereof, and includes a write-once-read-many (WORM) area where the information is written.

Another embodiment features a chromatographic system, which includes a chromatographic separation module; a memory component, which is attached to the chromatographic separation module, contains information related to the chromatographic separation module with respect to the entire lifetime thereof, and includes a write-once-read-many (WORM) area where the information is written; a detection module interfacing with the chromatographic separation module to generate chromatographic data; a data-processing component in signal communication with the memory component and the detection module to receive the chromatographic data, to process the received chromatographic data and to output the processed chromatographic data to the memory component; and a data transmission interface connecting the data-processing component to the memory component to transmit data therebetween.

A further embodiment provides a method, which includes the step of providing a chromatographic system including: a chromatographic separation module; a memory component attached to the chromatographic separation module; a detection module interfacing with the chromatographic separation module; a data-processing component in signal communication with both the memory component and the detection module; and a data transmission interface connecting the data-processing component to the memory component. The method further includes the steps of: generating chromatographic data with the detection module interfacing with the chromatographic separation module; receiving and processing the chromatographic data with the data-processing component; transmitting the processed chromatographic data from the data-processing component to the memory component via the data transmission interface; and storing the chromatographic data in the memory component.

Implementations may include one or more of the following features.

In some implementations, the memory component includes a semiconductor chip.

In some implementations, the memory component is embedded in the chromatographic separation module.

In some cases, the information includes manufacturing information of the chromatographic separation module.

In some cases, the information includes start-up and shut-down procedures of the chromatographic separation module.

In some cases, the information includes chains of custody and audit trails for the chromatographic separation module.

In some cases, the information includes real-time diagnostics and trouble-shooting information for the chromatographic separation module.

In some cases, the information includes information of instruments that have been utilized in conjunction with the chromatographic separation module.

In some cases, the information includes specifications of instruments permitted to be utilized in conjunction with the chromatographic separation module.

In some cases, the information includes chromatographic data generated during the lifetime of the chromatographic separation module.

In some cases, the information includes method parameters, calibration curves and application conditions associated with each of chromatographic runs by the chromatographic separation module during the lifetime thereof.

In some implementations, the processed chromatographic data is outputted to the memory component during a separation operation.

In some implementations, the detection module includes at least one mass spectrometer, at least one optical detection module, or a combination thereof.

In some implementations, the processed chromatographic data are extracted chromatograms of selected mass ranges.

In other implementations, the processed chromatographic data are chromatograms in single or multiple wavelength modes.

In some implementations, the at least one optical detection module is an absorption detector, a fluorescence detector, a Raman spectrometer, a nuclear magnetic resonance (NMR) spectrometer, an evaporative light scattering detection (ELSD) module, or any combination thereof.

In other implementations, the detection module includes a flame ionization detector, a conductivity-based detector, an electrochemical detector, a circular dichroism (CD) detector, or any combination thereof.

In some implementations, the data transmission interface includes at least one electrical bus, which is in electrical signal communication with the memory component and the data-processing component, and one example of such electrical bus is a Universal Serial Bus (USB) connector.

In some implementations, the chromatographic system is connected to a database server including a database having a record associated with the chromatographic separation module.

In some implementations, the record has a globally unique identifier (GUID) field identifying the chromatographic separation module.

In some implementations, the GUID is stored on the memory component.

In some implementations, the chromatographic data is ported to the database to be stored under the GUID.

In some implementations, the chromatographic data includes raw chromatographic data.

In some implementations, the database is an Oracle database, a Scientific Data Management System (SDMS), or any suitable relational database having a link to the GUID.

In some implementations, the database server includes a personal computer, a server computer, an electronic laboratory notebook (ELN), a mainframe computer, or any suitable informatics system.

In some implementations, the database server includes a network interface, which includes a wired or wireless network interface, or a combination thereof, and through the network interface, the record is accessed from any computers networked to the database server and by multiple users at the same time.

Other implementations, features and advantages are in the description, drawings and claims.

BRIEF DESCRIPTION OF THE DRAWINGS

In the drawings, same or like reference characters and numbers generally refer to same or like elements throughout different views. Also, the drawings are not necessarily to scale.

DETAILED DESCRIPTION

Some illustrative implementations will now be described with respect to FIGS. 1-4. In view of this description, modifications and alterations to these implementations will be apparent to one of ordinary skill in the art.

Figure 1:
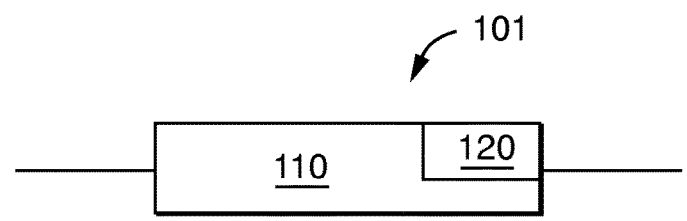
FIG. 1 is a schematic view of a chromatographic separation device, including a chromatographic separation module and a memory component attached to the chromatographic separation module.

Referring to FIG. 1, a chromatographic separation device 101 includes a chromatographic separation module 110 and a memory component 120 attached to the chromatographic separation column 110.

The chromatographic separation module 110 can be a liquid chromatography (LC), gas chromatography (GC) or a supercritical fluid chromatographic (SFC) separation module, and can be fabricated in any desired form, such as a column, a tile, a chip or a cartridge, packed with separation media. The separation media can be either fully porous or superficially porous particles, or any suitable materials of any suitable sizes.

The memory component 120 contains information related to the chromatographic separation module 110 and chromatographic data produced during the entire lifetime of the chromatographic separation module 110. In some embodiments, the memory component 120 includes a WORM area, where information, once written, cannot be deleted or modified. The memory component 120 can have a storage capacity up to 16 GB or greater and can be any commercially available memory device, such as a SD card, a Compact Flash card, etc. The data and information can be stored in a magnetic strip, a semiconductor chip, or any other suitable medium, which has enough capacity for chromatographic data generated during the entire lifetime of the chromatographic separation module 110, at least, in a compressed format.

In some embodiments, the information stored on the memory component 120 includes, for example, manufacturing information of the chromatographic separation module 110, such as manufacturing lot, serial numbers, raw materials and chemicals used in fabrication, packing medium, testing method, test results, and/or quality control data. The information also contains, for example, full use history of the chromatographic separation module 110, including the number of hours in use, sterilization cycles, and details on each sample injection (e.g., pressure and temperature profiles). The information further includes method parameters, calibration curves and application conditions (e.g., flow rates, gradients, solvents, etc.) associated with each separation run by the chromatographic separation module 110.

Other information stored on the memory component 120 includes, by way of example but not limited to, proper start-up and shut-down procedures of the chromatographic separation module 110, chains of custody and audit trails, real-time diagnostics and trouble-shooting information, information of instruments that have been utilized in conjunction with the chromatographic separation module, and specifications of instruments that are permitted to be utilized in conjunction with the chromatographic separation module.

In some implementations, the chromatographic data generated during the entire lifetime of the chromatographic separation module 110 is stored on the memory component 120 in a compressed form. The memory component 120, with its capacity of up to 16 GB or greater and use of a compressed format, can capture all sample injections that the chromatographic separation device 110 lasts for its lifetime. Typically, a chromatographic separation column can last 10,000 injections, each injection produces about 1000 to 2000 data points in a compressed dataset, and each data point takes about 4 bytes of memory space. Thus, the total number of data points generated during the lifetime of a chromatographic separation column is about $10^7$, which requires a memory space of about $4*10^7$ bytes. Apparently, a 16 GB—$10^{10}$ bytes—memory component is capable of storing all data points produced during the entire lifetime of a chromatographic separation column.

Figure 2:
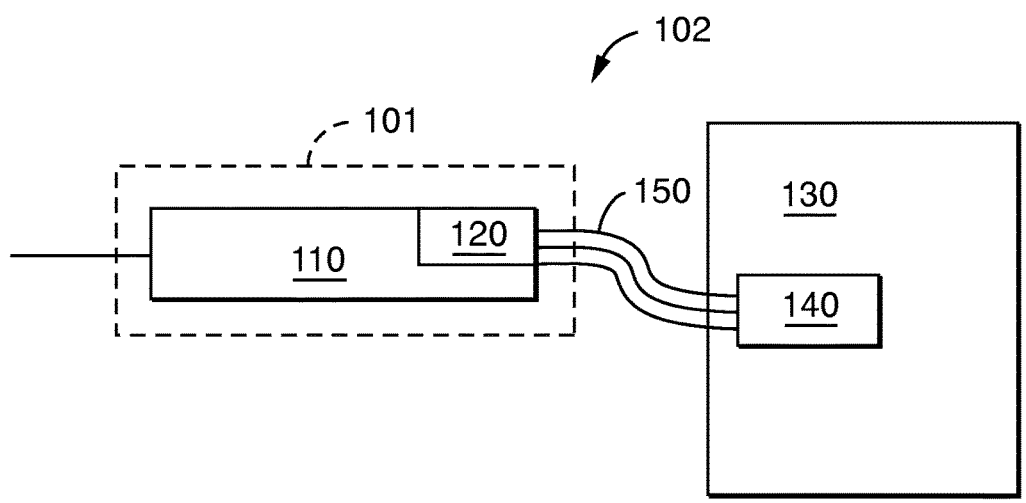
FIG. 2 is a schematic view of a chromatographic system, including the chromatographic separation device of FIG. 1, a detection module, a data-processing component and a data transmission interface.

Turning now to FIG. 2, a chromatographic system 102 includes the chromatographic separation device 101 of FIG. 1, which includes the chromatographic separation module 110 and the memory component 120, a detection module 130, a data-processing component 140, and a data transmission interface 150.

The detection module 130 is interfacing with the chromatographic separation module 110 to generate chromatographic data. The detection module 130 can be a mass-spectrometry-based detection module, e.g., an electro-spray ionization (ESI) mass spectrometer, or a detection module based on optical technologies, such as ultraviolet (UV), infrared (IR), or UV-visible absorption methods, fluorescence detection methods, NMR spectroscopy, ELSD, or any combination thereof. Other detection methods may also be used, e.g., flame ionization, conductivity, electrochemical detection, and CD.

The data-processing component 140, in signal communication with the memory component 120 and the detection module 130, receives the chromatographic data generated from the detection module 130, processes the received chromatographic data and writes the processed chromatographic data to the WORM area of the memory component 120. In some cases, the processed chromatographic data are extracted chromatograms of selected mass ranges, where one or more mass-over-charge values or intensity data thereof, representing one or more analytes of interest, are extracted from the entire dataset of a chromatographic separation run. In other cases, the processed chromatographic data are single- or multiple-wavelength chromatograms where one or more particular species are recovered from an entire chromatographic dataset.

In some implementations, the processed chromatographic data can be compressed and encrypted before being sent to the memory component 120. As previously described, the memory component 120 has a storage capacity for the processed chromatographic data generated during the entire lifetime of the chromatographic separation module 110, at least, in a compressed format. In some implementations, the data-processing component 140 is a microprocessor which can be disposed within the detection module 130.

The data transmission interface 150 is in signal communication with both the memory component 120 and the data-processing component 140 to transmit data therebetween. In some implementations, the data transmission interface 150 can include an electrical bus, for example, a Universal Serial Bus (USB) connector. In other implementations, more than one electrical bus can be used to connect the data-processing component 140 to the memory component 120 to transmit data therebetween.

Figure 3A:
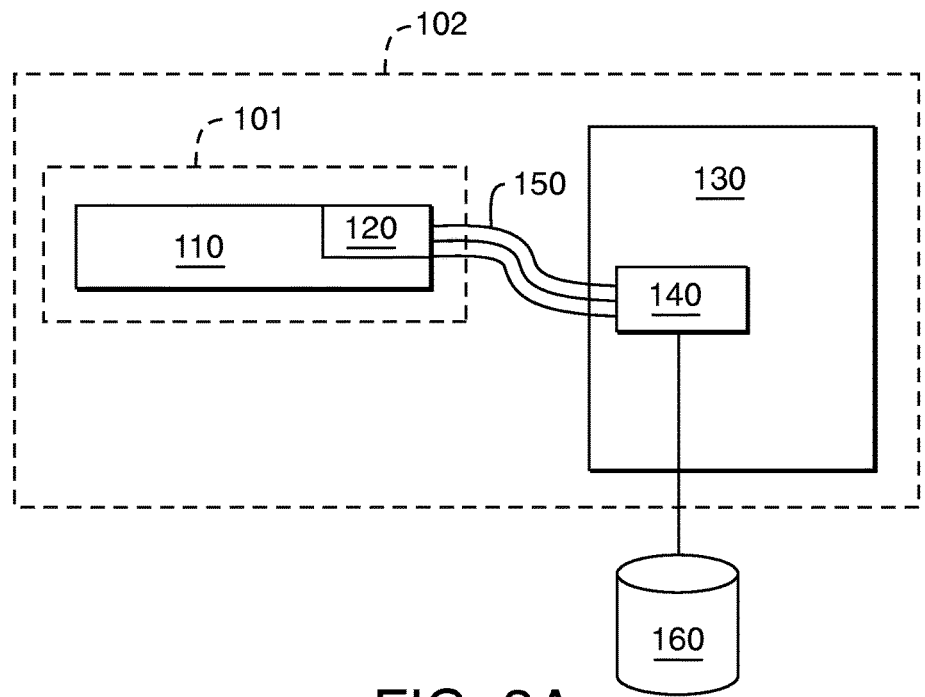
FIG. 3A is a schematic view of a system, including the chromatographic system of FIG. 2 and a database server.

Turning next to FIG. 3A, a system 103 includes the chromatographic system 102 of FIG. 2 and a database server 160.

The chromatographic system 102 includes the chromatographic separation device 101 of FIG. 1, which includes the chromatographic separation module 110 and the memory component 120, a detection module 130 interfacing with the chromatographic separation module 110 to generate chromatographic data, a data-processing component 140 in signal communication with the memory component 120 and the detection module 130 to receive the chromatographic data, to process the received chromatographic data and to write the processed chromatographic data to the WORM area of the memory component 120; and a data transmission interface 150 connecting the data-processing component 140 to the memory component 120 to transmit data therebetween.

As shown in FIG. 3A, the chromatographic system 102 is connected to the database server 160 having a database installed thereon. The database contains a record associated with the chromatographic separation module 110 and has an identifier (ID) or a GUID field that identifies the chromatographic separation module 110 as a unique globe entity. The GUID can be created when the chromatographic separation module 110 is being run and connected to the database the first time, and thereafter chromatographic data can be ported to the database to be stored in the record under the ID or GUID.

As described above, chromatographic data generated from the detection module 130 can be processed by the data-processing component 140, and the processed chromatographic data can be extracted chromatograms of either selected mass ranges or selected wavelengths.

Figure 3B:
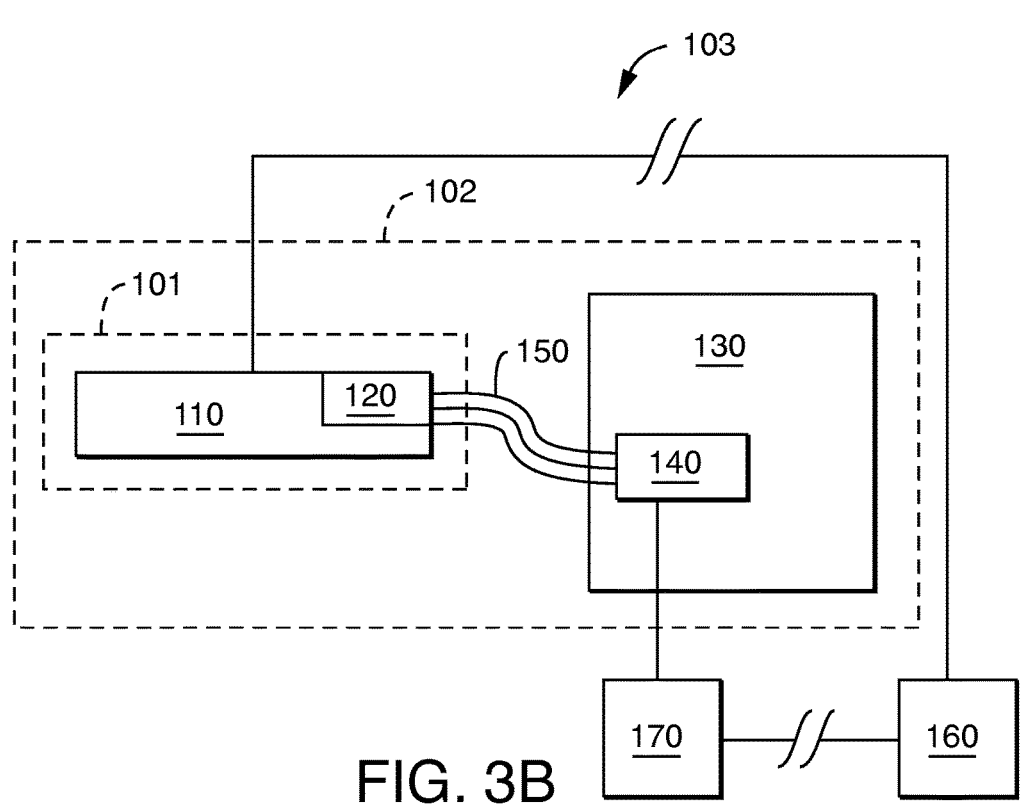
FIG. 3B is another schematic view of a system, including the chromatographic system of FIG. 2 and a database server.

The processed chromatographic data can be ported to the database server 160 directly from the data-processing component 140 in real-time or online, that is, as raw data are being acquired, as shown in FIG. 3A, or can be transferred to the database server 160 in non-real-time or offline, i.e., when the data acquisition is done, as shown in FIG. 3B. Transferring data to the database server 160 offline (as shown in FIG. 3B) can be done in, e.g., two ways: 1) the processed chromatographic data is written by the data-processing component 140 to the memory component 120 in a compressed form, when raw data are being acquired, and the compressed data is ported from the memory component 120 to the database server 160, when the data acquisition is done; and 2) the processed chromatographic data is sent by the data-processing component 140 to an intermediate data buffer 170 to be stored in a raw (uncompressed) form, when raw data are being acquired, and the raw data are ported from the intermediate data buffer 170 to the database server 160, when the data acquisition is done. One example of such an intermediate data buffer is a LAC/E$^{32}$ Acquisition Sever, available from Waters Corporation, Massachusetts, US. In either way of transferring data offline, a combination of hardware and software is used to capture data and results from the chromatographic system 102 given the appropriate access rights. In some implementations, the raw data form is preferred as it complies with US Federal Good Laboratory Practice (GLP) regulations. The processed chromatographic data can also be ported, either online or offline, to a flat file system having a link to the GUID.

The database server 160 can be a personal computer, a server computer, an electronic laboratory notebook (ELN), a mainframe computer, or any suitable informatics system. The database can be any information/data management system, e.g., an Oracle database, available form Oracle Corporation, California, US, a SDMS, available form Waters Corporation, Massachusetts, US, or any suitable relational database that has a GUID field associated with the chromatographic separation module 110.

In some embodiments, the database server 160 can include a wired or wireless network interface so that the records stored in the database can be accessed from any computers networked to the database server 160 and viewed by multiple users at the same time via the network interface.

Figure 4:
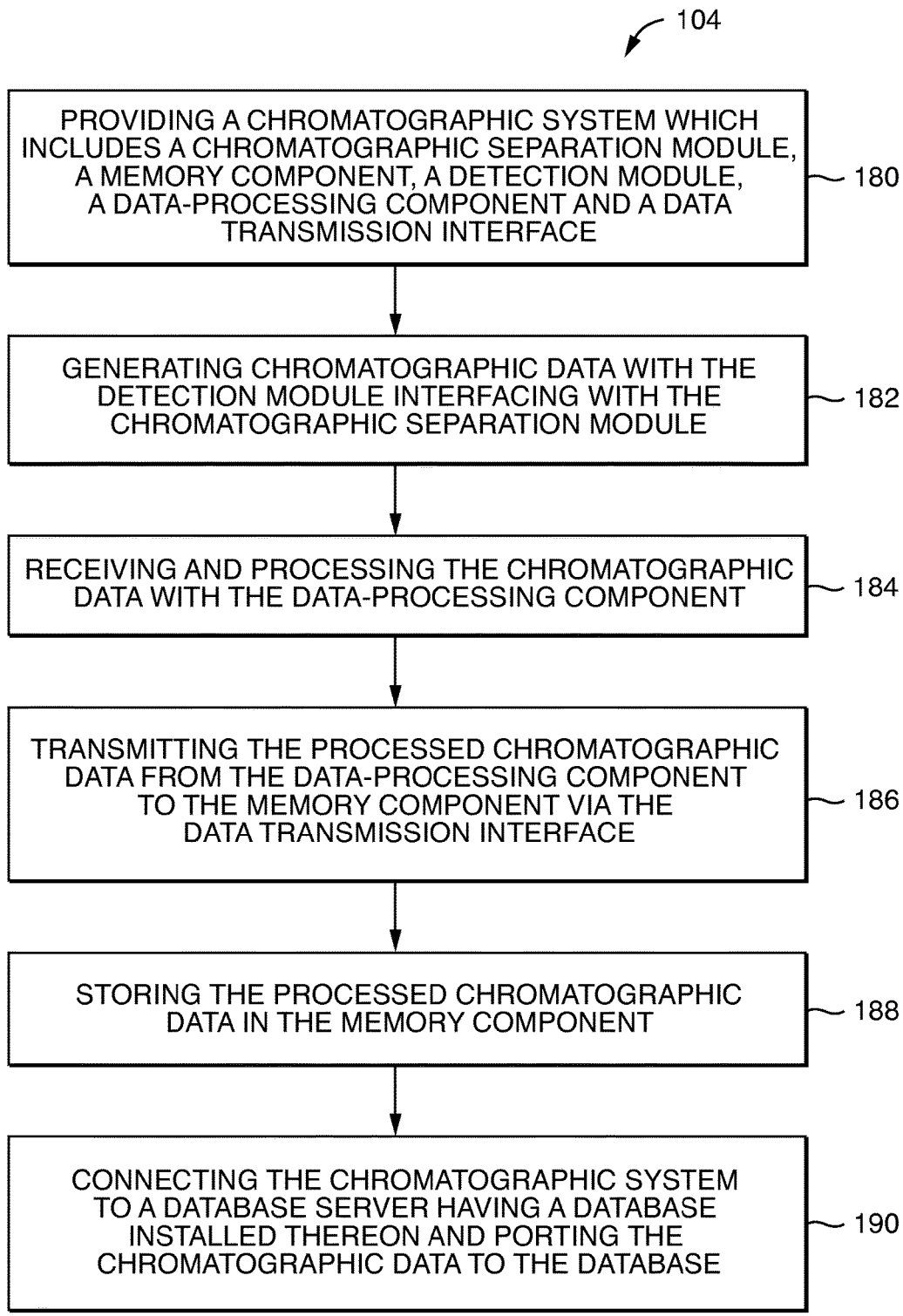
FIG. 4 is a flow diagram of a method for managing data generated during the lifetime of the chromatographic separation device of FIG. 1.

FIG. 4 is a flow diagram 104 of a method for managing data generated during the entire lifetime of the chromatographic separation device of FIG. 1.

The method includes the step of providing (180) a chromatographic system, which includes a chromatographic separation module, a memory component, a detection module, a data-processing component and a data transmission interface; generating (182) chromatographic data with the detection module interfacing with the chromatographic separation module; receiving and processing (184) the chromatographic data with the data-processing component; transmitting (186) the processed chromatographic data from the data-processing component to the memory component via the data transmission interface; and storing (188) the chromatographic data in the memory component.

The step of processing (184) the chromatographic data includes extracting the chromatographic data, wherein the extracted chromatographic data can be either chromatograms of selected mass ranges or chromatograms in single or multiple wavelength modes.

The method further includes the step (190) of connecting the chromatographic system to a database server having a database installed thereon and porting the chromatographic data to the database.

Although a number of implementations have been described in detail above, other modifications, variations and implementations are possible in light of the foregoing teaching.

For example, though, as illustrated in FIG. 2, the memory component 120 is attached to the chromatographic separation module 110, it can be embedded inside the chromatographic separation module 110. The memory component 120 can also be attached to any equipment component included in the chromatographic system 102, e.g., a sample tray in an auto-sampler.

For example, though, as depicted in FIG. 2, the electrical bus 150 is used to transmit data between the data-processing component 140 and the memory component 120, other data transmission interfaces can also be used, depending on the medium in which the data stored in the memory component 120, examples of which include, but are not limited to, bar code reader, a magnetic strip reader, a radio transponder, an inductive loop, ultra-sonic, infra-red, direct connection, an optical detector, electrical impulse detector or a data bus socket, or other means are known to those skilled in the art.

Accordingly, the invention is to be defined not by the preceding illustrative description but instead by the scope of the following claims.

What is claimed is:

1. A chromatographic system comprising:
a chromatographic separation module;
a memory storage component attached to the chromatographic separation module, the memory storage component containing information related to use history of the chromatographic separation module with respect to the entire lifetime thereof and consisting of a write-once-read-many (WORM) area where the information is written and where the information, once written, cannot be deleted or modified, wherein all the information stored by the chromatographic system related to the use history of the chromatographic separation module with respect to the entire lifetime thereof is stored in the WORM area;
a detector interfacing with the chromatographic separation module to generate chromatographic data;
a data processor in signal communication with the memory storage component and the detector to receive the chromatographic data, to process the received chromatographic data, and to output processed chromatographic data to the memory storage component; and
a data transmission interface connecting the data processor to the memory storage component to transmit data therebetween.

2. The chromatographic system of claim 1, wherein the processed chromatographic data is outputted to the memory storage component during a separation operation.

3. The chromatographic system of claim 1, wherein the detector comprises at least one mass spectrometer, at least one optical detector, or a combination thereof.

4. The chromatographic system of claim 3, wherein the processed chromatographic data are extracted chromatograms of selected mass ranges.

5. The chromatographic system of claim 3, wherein the processed chromatographic data are chromatograms in single or multiple wavelength modes.

6. The chromatographic system of claim 3, wherein the at least one optical detector is an absorption detector, a fluorescence detector, a Raman spectrometer, a nuclear magnetic resonance (NMR) spectrometer, an evaporative light scattering detector (ELSD), or any combination thereof.

7. The chromatographic system of claim 1, wherein the detector comprises a flame ionization detector, a conductivity-based detector, an electrochemical detector, a circular dichroism (CD) detector, or any combination thereof.

8. The chromatographic system of claim 1, wherein the data transmission interface comprises at least one electrical bus.

9. The chromatographic system of claim 8, wherein the electrical bus is in electrical signal communication with the memory storage component and the data-processing component.

10. The chromatographic system of claim 8, wherein the electrical bus is a Universal Serial Bus (USB) connector.

11. The chromatographic system of claim 1 being connected to a database server comprising a database having a record associated with the chromatographic separation module.

12. The chromatographic system of claim 11, wherein the record comprises a globally unique identifier (GUID) field identifying the chromatographic separation module.

13. The chromatographic system of claim 12, wherein the GUID is stored on the memory storage component.

14. The chromatographic system of claim 12, wherein the chromatographic data is ported to the database to be stored under the GUID.

15. The chromatographic system of claim 14, wherein the chromatographic data comprises raw chromatographic data.

16. The chromatographic system of claim 12, wherein the database is any of an Oracle database, a Scientific Data Management System (SDMS), or a relational database having a link to the GUID.

17. The chromatographic system of claim 11, wherein the database server comprises any of a personal computer, a server computer, an electronic laboratory notebook (ELN), a mainframe computer, or an informatics system.

18. The chromatographic system of claim 11, wherein the database server comprises a network interface.

19. The chromatographic system of claim 18, wherein the network interface comprises a wired or wireless network interface, or a combination thereof.

20. The chromatographic system of claim 18, wherein the record is accessed from any computers networked to the database server via the network interface.

21. The chromatographic system of claim 18, wherein the record is accessed by multiple users at the same time via the network interface.

22. The chromatographic system of claim 1, wherein the information is stored in a compressed format.

23. A chromatographic method comprising:
providing a chromatographic system including:
- a chromatographic separation module;
- a memory storage component attached to the chromatographic separation module, the memory storage component containing all stored information related to use history of the chromatographic separation module with respect to the entire lifetime thereof and consisting of a write-once-read-many (WORM) area where the information is written and where the information, once written, cannot be deleted or modified;
- a detector interfacing with the chromatographic separation module to generate chromatographic data;
- a data processor in signal communication with the memory storage component and the detector to receive the chromatographic data, to process the received chromatographic data, and to output processed chromatographic data to the memory storage component; and
- a data transmission interface connecting the data processor to the memory storage component to transmit data therebetween; and storing throughout the entire lifetime of use, by the chromatographic system, information related to use history of the chromatographic separation module with respect to the entire lifetime thereof, wherein all the information stored by the chromatographic system related to use history is stored in the WORM area.

24. The chromatographic method of claim 23, further comprising compressing, by the data processor, the information related to use history of the chromatographic separation module with respect to the entire lifetime thereof.

* * * * *